US011950948B2

United States Patent
Williams et al.

(10) Patent No.: US 11,950,948 B2
(45) Date of Patent: Apr. 9, 2024

(54) SYSTEMS AND METHODS FOR MITIGATING IMAGING ARTIFACTS

(71) Applicant: HOLOGIC, INC., Marlborough, MA (US)

(72) Inventors: Cornell Lee Williams, Marlborough, MA (US); Brad Polischuk, Marlborough, MA (US)

(73) Assignee: HOLOGIC, INC., Marlborough, MA (US)

( * ) Notice: Subject to any disclaimer, the term of this patent is extended or adjusted under 35 U.S.C. 154(b) by 461 days.

(21) Appl. No.: 17/277,013

(22) PCT Filed: Sep. 17, 2019

(86) PCT No.: PCT/US2019/051473
§ 371 (c)(1),
(2) Date: Mar. 17, 2021

(87) PCT Pub. No.: WO2020/061015
PCT Pub. Date: Mar. 26, 2020

(65) Prior Publication Data
US 2022/0031275 A1 Feb. 3, 2022

Related U.S. Application Data

(60) Provisional application No. 62/732,746, filed on Sep. 18, 2018.

(51) Int. Cl.
*A61B 6/00* (2006.01)
*G06T 5/50* (2006.01)
*G06T 7/00* (2017.01)

(52) U.S. Cl.
CPC ............ *A61B 6/5258* (2013.01); *A61B 6/542* (2013.01); *G06T 5/50* (2013.01); *G06T 7/0012* (2013.01); *G06T 2207/10116* (2013.01)

(58) Field of Classification Search
CPC ....... A61B 6/5258; A61B 6/542; A61B 6/488; A61B 6/545; G06T 5/50; G06T 7/0012;
(Continued)

(56) References Cited

U.S. PATENT DOCUMENTS 6,744,848 B2 6/2004 Stanton et al.
7,245,694 B2 7/2007 Jing et al.
(Continued)

FOREIGN PATENT DOCUMENTS

JP 2002-085391 A 3/2002
JP 2010-082254 A 4/2010
(Continued)

OTHER PUBLICATIONS

International Search Report and Written Opinion of the International Searching Authority for International Patent Application No. PCT/US2019/051473 dated Nov. 19, 2019, 10 pages.
(Continued)

*Primary Examiner* — Dhaval V Patel
(74) *Attorney, Agent, or Firm* — Merchant & Gould P.C.

(57) ABSTRACT

Radiographic imaging techniques include the use of an exposure sequence having a plurality of specimen exposure windows. The plurality of specimen exposure windows have a total exposure time period that satisfies a desired exposure time. The plurality of exposure frames resulting from the plurality of specimen exposure windows are summed to form an output frame. The output frame is provided as output.

20 Claims, 7 Drawing Sheets

(58) Field of Classification Search
CPC .......... G06T 2207/10116; H04N 25/46; H04N 25/63; H04N 5/32; H04N 25/53
See application file for complete search history.

(56) References Cited

U.S. PATENT DOCUMENTS

| | | |
|---|---|---|
| 2010/0202933 A1 | 1/2010 | Topfer et al. |
| 2013/0272494 A1 | 10/2013 | DeFreitas et al. |
| 2014/0064458 A1* | 3/2014 | Jobst ...................... A61B 6/585 |
| | | 378/207 |
| 2015/0281604 A1 | 10/2015 | Shah et al. |
| 2017/0065240 A1* | 3/2017 | Zou ...................... G01N 23/087 |
| 2017/0374295 A1* | 12/2017 | Topfer ................... H04N 25/63 |
| 2019/0246999 A1* | 8/2019 | Liu ........................ A61B 6/487 |

FOREIGN PATENT DOCUMENTS

| | | |
|---|---|---|
| JP | 2014-090960 A | 5/2014 |
| JP | 2014-168602 A | 9/2014 |
| JP | 2016-527490 A | 9/2016 |
| WO | 2008/153085 A1 | 12/2008 |
| WO | 2011/048629 | 4/2011 |
| WO | 2018/085719 A1 | 5/2018 |

OTHER PUBLICATIONS

PCT International Preliminary Report on Patentability in Application PCT/US2019/051473, dated Apr. 1, 2021, 8 pages.

* cited by examiner

SYSTEMS AND METHODS FOR MITIGATING IMAGING ARTIFACTS

CROSS-REFERENCE TO RELATED APPLICATION

This application is a National Stage Application of PCT/US2019/051473, filed Sep. 17, 2019, which claims priority to and the benefit of U.S. Provisional Patent Application No. 62/732,746, which is titled "SYSTEMS AND METHODS FOR MITIGATING IMAGING ARTIFACTS", filed Sep. 18, 2018, the disclosures of which i-s are hereby incorporated by reference herein in their entireties for any and all purposes. To the extent appropriate, a claim of priority is made to each of the above disclosed applications.

BACKGROUND

Specimen radiography systems are used to image tissue specimens for diagnosis in medical environments, such as operating rooms and clinics. Specimen radiography systems vary in size. Some are designed primarily for imaging small specimens. Such systems typically have small detector Regions of Interest (ROI) and use low to medium exposure techniques. Certain specimen radiography systems are designed to allow for a wide range of specimen sample sizes, including the full mammary specimens via mastectomy. In order to allow a wide range of specimens, such systems typically include enhanced large detector ROI and use higher exposure techniques. However, the use of higher exposure techniques can cause undesirable artifacts to appear in resulting images.

SUMMARY

In some examples, there is a radiographic imaging system. The radiographic imaging system includes a specimen holder, an x-ray source, an x-ray detector, and a controller. In some examples, the x-ray detector is configured to simultaneously output a first reading from a first portion of the x-ray detector and second reading from a second portion of the x-ray detector. In some examples, the controller includes at least one processor and memory. In some examples, the memory stores instructions that, when executed by the at least one processor, cause the radiographic imaging system to perform a set of operations. The set of operations include: determining a desired exposure time; defining an exposure sequence having a plurality of specimen exposure windows, wherein each specimen exposure window of the plurality of specimen exposure windows has an exposure time period, and wherein a total of the exposure time periods of the plurality of specimen exposure windows satisfies the desired exposure time; controlling the x-ray source and the x-ray detector to obtain at least one exposure reference frame; controlling the x-ray source and the x-ray detector using the exposure sequence to obtain a plurality of exposure frames from the x-ray detector; forming a plurality of corrected exposure frames by modifying the plurality of exposure frames using the at least one exposure reference frame; summing the plurality of corrected exposure frames to form an output frame; and providing the output frame as output.

In one or more of the foregoing radiographic imaging systems, the set of operations further includes binning a group of pixels of the x-ray detector. In one or more of the foregoing radiographic imaging systems, the set of operations further includes selectively modifying a size of the group of pixels on which the binning is performed. In one or more of the foregoing radiographic imaging systems, there is a display and the set of operations includes providing the output frame as output using the display. In one or more of the foregoing radiographic imaging systems, the x-ray source is configured to operate with a current of less than 1.5 milliamps. In one or more of the foregoing radiographic imaging systems, the x-ray source is stationary. In one or more of the foregoing radiographic imaging systems, the at least one exposure reference frame comprises at least two exposure reference frames; the set of operations further includes forming a combined exposure reference frame from the at least two exposure reference frames; and modifying the plurality of exposure frames using the at least one exposure reference frame includes subtracting the combined exposure reference frame from each of the plurality of exposure frames. In one or more of the foregoing radiographic imaging systems, forming the plurality of corrected exposure frames includes subtracting the at least one exposure reference frame from each of the plurality of exposure frames. In one or more of the foregoing radiographic imaging systems, summing the plurality of corrected exposure frames to form an output frame includes summing pixel values of respective pixels of the plurality of corrected exposure frames to form a respective summed pixel in the output frame.

In some examples, there is a method for performing radiographic imaging. The method includes determining, using a controller of an x-ray imaging system, a desired exposure time; defining, using the controller of the x-ray imaging system, an exposure sequence having a plurality of specimen exposure windows, wherein each specimen exposure window of the plurality of specimen exposure windows has an exposure time period, and wherein a total of the exposure time periods of the plurality of specimen exposure windows satisfies the desired exposure time; controlling, using the controller of the x-ray imaging system, an x-ray source and an x-ray detector of the x-ray imaging system to obtain at least one exposure reference frame; controlling, using the controller of the x-ray imaging system, the x-ray source and the x-ray detector to perform radiographic imaging using the exposure sequence to obtain a plurality of exposure frames from the x-ray detector; forming, using the controller of the x-ray imaging system, a plurality of corrected exposure frames by modifying the plurality of exposure frames using the at least one exposure reference frame; summing, using the controller of the x-ray imaging system, the plurality of corrected exposure frames to form an output frame; and providing, using the controller of the x-ray imaging system, the output frame as output.

In some example methods, forming the plurality of corrected exposure frames comprises: subtracting the at least one exposure reference frame from each of the plurality of exposure frames. In one or more of the foregoing methods, the at least one exposure reference frame comprises at least two exposure reference frames; the method further includes forming a combined exposure reference frame from the at least two exposure reference frames; and wherein forming the plurality of corrected exposure frames includes subtracting the combined exposure reference frame from each of the plurality of exposure frames. In one or more of the foregoing methods, obtaining the at least one exposure reference frame includes obtaining the at least one exposure reference frame from a radiographic imaging system. In one or more of the foregoing methods, obtaining the at least one exposure reference frame occurs before performing the radiographic imaging on the specimen. In one or more of the foregoing methods, the desired exposure time is at least 11.0 seconds; and performing the radiographic imaging comprises energizing an x-ray source of the radiographic imaging system with a current of less than 1.5 milliamps. In one or more of the foregoing methods, the desired exposure time is between 7.0 seconds and 20.0 seconds; and the exposure time period of each specimen exposure window of the plurality of specimen exposure windows is between 0.7 seconds and 2.0 seconds. In one or more of the foregoing methods, performing the radiographic imaging comprises performing radiographic imaging on a breast tissue specimen. In one or more of the foregoing methods, performing the radiographic imaging includes: simultaneously reading first sensor portion output data from a first portion of an x-ray detector of the radiographic imaging system and second sensor portion output data from a second portion of the x-ray detector; and at least one of the plurality of exposure frames includes the first sensor portion output data and the second sensor portion output data. In one or more of the foregoing methods, the method further includes performing, using the controller of the x-ray imaging system, radiographic imaging to obtain a long exposure frame having an exposure time of more than ten seconds from the radiographic imaging system; obtaining, using the controller of the x-ray imaging system, a long exposure reference frame; and forming, using the controller of the x-ray imaging system, a long exposure corrected frame using the long exposure frame and the long exposure reference frame, and the long exposure corrected frame comprises a virtual line artifact.

In some examples, there is a computer-readable medium comprising instructions that, when executed by one or more processors, cause the performance of one or more of the foregoing methods.

In some examples, there is a method including: obtaining a plurality of exposure frames from a radiographic imaging system; forming a plurality of corrected exposure frames by modifying the plurality of exposure frames using at least one exposure reference frame; forming an output frame, wherein forming the output frame includes summing the plurality of corrected exposure frames; and providing the output frame as output.

In some examples, obtaining the plurality of exposure frames from the radiographic imaging system includes causing the radiographic imaging system capture the plurality of exposure frames according to an exposure sequence defining a plurality of specimen exposure windows. In some examples, each specimen exposure window of the plurality of specimen exposure windows has an exposure time period. In some examples, a total exposure time period of the exposure time periods of the plurality of specimen exposure windows satisfies a desired exposure time. In some examples, the desired exposure time is at least 11.0 seconds. In some examples, obtaining the plurality of exposure frames from the radiographic imaging system includes obtaining the plurality of exposure frames from a radiographic imaging system having an x-ray source configured to draw a current of less than 1.5 milliamps.

DETAILED DESCRIPTION

Long x-ray exposures of specimens are advantageous because they allow for a relatively higher signal to noise ratio compared to shorter exposures. X-ray exposure times are a function of the current of the x-ray source. For example, a first radiographic imaging system having an x-ray source running at 200 milliamps (mA) is capable of delivering 20 milliamp-seconds (mAs) in 0.1 seconds. Whereas a second radiographic imaging system having an x-ray source running at only 1 mA would take 20 seconds to deliver the same 20 mAs.

In radiographic imaging systems, when an x-ray detector exposure window extends beyond approximately 10 seconds, dark leakage currents of the radiography detector structure are not compensated fully. Such leakage can result in undesirable visual artifacts in the output from the detector. Such artifacts include areas of non-uniformity, such as virtual-line artifacts. Virtual-line artifacts can appear where top and bottom portions of x-ray detectors meet. Such lines can appear due to, for example, asymmetric charge leaking onto the source lines relative to Thin-Film Transistor (TFT) top and bottom portions of the x-ray detector during simultaneous readout of the top and bottom portions. In order to mitigate the formation of such visual artifacts while still allowing for long exposure times, examples herein can split a long exposure window into multiple, shorter exposure windows. The frames resulting from those shorter exposure windows are combined to produce an output frame with reduced visual artifacts. Such a technique can be used to reduce the occurrence of visual artifacts in the output of radiographic imaging systems having low-current x-ray sources.

The methods and systems described herein may be used to substantially reduce artifacts. Disclosed techniques are still advantageous in producing diagnostically relevant images where the effects of artifacts are reduced such that the images obtained are beneficial to medical personnel for making proper determinations, evaluations, and diagnoses. Although the specification describes correcting exposure frames to mitigate visual artifacts, such visual artifacts need not be completely eliminated.

Figure 1:
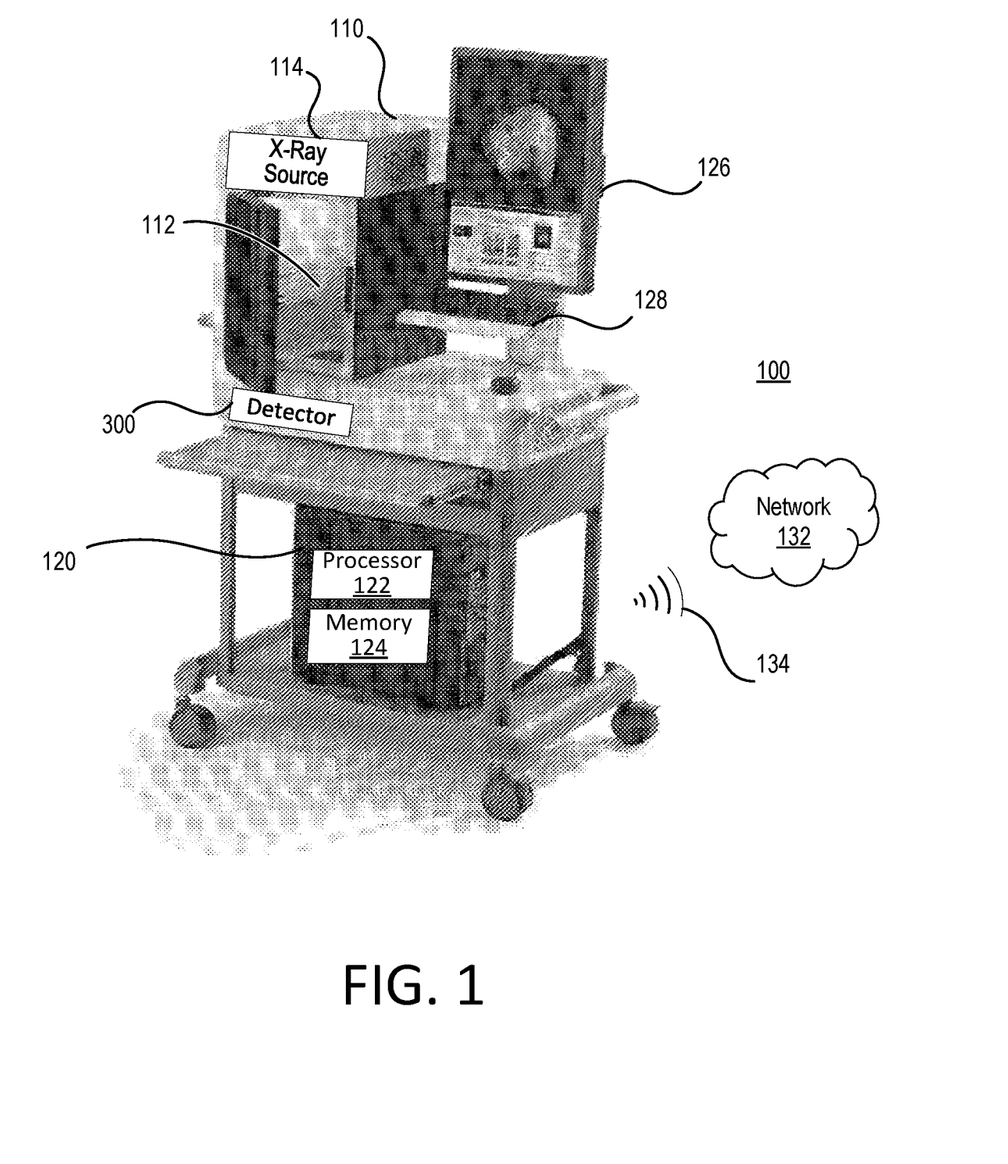
FIG. 1 illustrates an example radiographic imaging system.

FIG. 1 illustrates an example radiographic imaging system 100. The radiographic imaging system 100 includes a cabinet 110 that is configured for receiving and imaging a specimen, such as a breast tissue specimen obtained from a biopsy or as a surgical specimen. A clinician can manually place the specimen in a specimen holder 112 of the cabinet 110 for imaging. The specimen holder 112 is a portion of the cabinet 110 that receives and holds the specimen for imaging and can include adjustable shelves or drawers for holding the specimen at various heights within the cabinet 110. The specimen holder 112 disposes the specimen between an x-ray source 114 and an x-ray detector 300 of the cabinet 110. The x-ray source 114 emits an x-ray beam when energized and, in many examples, may be an x-ray tube. In an example, the x-ray source 114 is stationary. For instance, the x-ray source 114 is configured within the radiographic imaging system 100 to be stationary during imaging (e.g., as opposed to a movable x-ray source that may be found in tomography systems).

The x-ray detector 300 receives x-ray energy and generates output frames based thereon. The x-ray detector 300 can take any of a variety of different forms, but is generally one of two different types of detectors: (1) a detector in which direct methods are used to convert x-rays into an electric charge, and (2) a detector in which indirect methods are used. Both direct-conversion and indirect-conversion detectors accumulate and store the electronic charges received during x-ray exposure. In direct-conversion detectors, an x-ray photoconductor (e.g., amorphous selenium) directly converts x-ray photons into an electric charge. In indirect-conversion detectors, scintillators convert x-ray energy into visible light, which is then converted into an electronic charge using photodetectors, such as amorphous silicon photodiode arrays or CCDs (Charge-Coupled Devices). In many examples, the x-ray detector 300 is divided into an array of M rows by N columns of detector pixels. For example, a mammography detector may include 4096 rows and 3584 channels per row. An example x-ray detector 300 is shown in more detail in relation to FIG. 3.

The controller 120 is a computing device component of the radiographic imaging system 100 that controls various aspects of the radiographic imaging system 100. In examples, the controller 120 selectively energizes the x-ray source 114 (e.g., in cooperation with an x-ray state machine thereof), controls the x-ray detector 300, obtains a frame from the x-ray detector 300, processes the frame from the x-ray detector 300, or provides the frame as output. In some examples, the controller 120 defines one or more exposure windows and one or more reference windows as described herein. In examples, the controller 120 is programmed with an x-ray state machine that controls the x-ray source 114. As illustrated, the controller 120 includes a processor 122, memory 124, a display 126, and an input device 128. The processor 122 is a computing processor, such as one or more CPUs (Central Processing Units). The memory 124 is a computer-readable storage medium (e.g., disk-based or solid state memory). The memory 124 can be a transitory or non-transitory computer-readable storage medium. The memory 124 can store software instructions and data. The instructions can, when executed by the processor 122, cause the processor 122 to control operations of the radiographic imaging system 100 and perform one or more operations described herein (e.g., one or more operations described herein in relation to FIG. 9). The display 126 is one or more components with which the radiographic imaging system 100 can provide visual output to a user. In the illustrated example, the display 126 takes the form of an LCD (Liquid Crystal Display) screen, though other display technology can be used. The input device 128 is one or more components over which the radiographic imaging system 100 can receive input from a user. The input device 128 includes one or more of a mouse, keyboard, or touch screen, among other devices directly or indirectly coupled to the radiographic imaging system 100.

The controller 120 and/or one or more other components of the radiographic imaging system 100 is connected to a network 132 via communication link 134. The network 132 is a communication network over which a plurality of computing devices can transfer data or otherwise communicate. The network 132 can take any of a variety of different forms. In some examples, the network 132 can include a common area network for node-to-node communication among different components of the radiographic imaging system 100 or a local area network (e.g., a local area network of the hospital or clinic having the radiographic imaging system). The communication link 134 is a connection to the network 132 suitable for the transfer of data. The communication link 134 can be wired (e.g., an Ethernet connection) or wireless (e.g., a WI-FI or BLUETOOTH connection). In an example, the controller 120 is configured to perform Automatic Exposure Control (AEC), which is described in greater detail in relation to FIG. 2.

Figure 2:
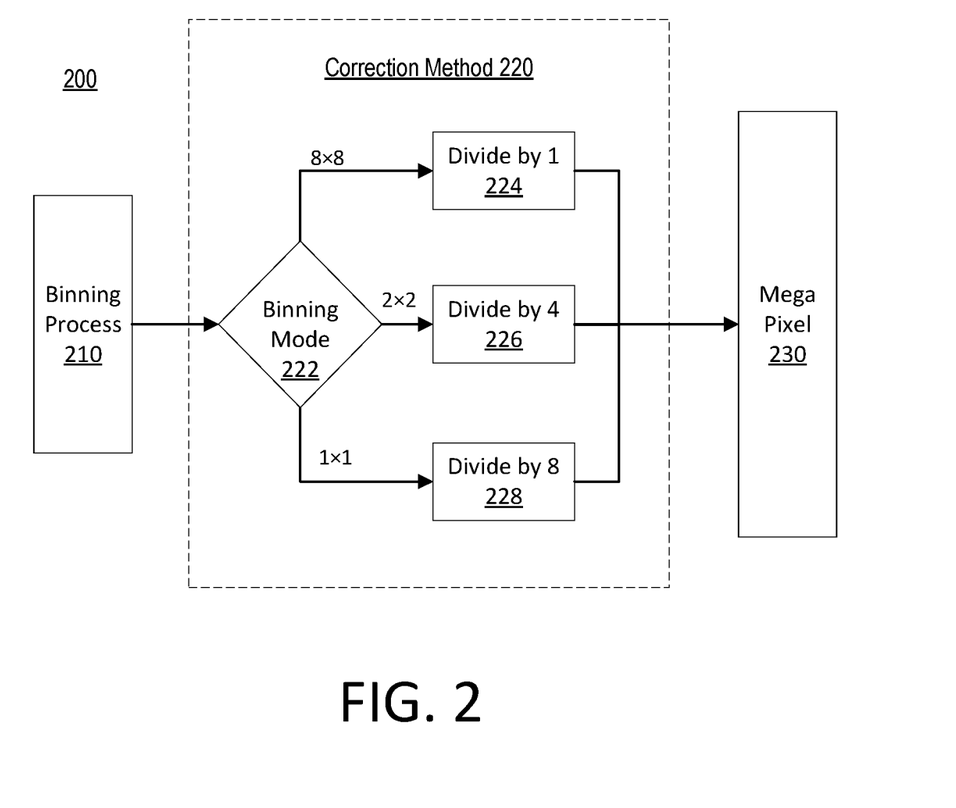
FIG. 2 illustrates a selective binning process for use in a radiographic imaging system.

FIG. 2 illustrates a selective binning process 200 that includes a correction method 220 that corrects for different binning modes used in the binning process 210 when producing a mega pixel 230. In general, the binning process 210 reduces the spatial resolution of the x-ray detector 300 by treating groups of imaging data (e.g., typically pixels) as being part of a same "bin" of imaging data. For example, in a four pixel binning process 210, the output of each set of four pixel positions in the x-ray detector 300 are treated as being a single pixel. For instance, the values of the four pixels (e.g., a 2×2 group of adjacent pixels) are averaged together or are otherwise combined for further frame processing or output. As a non-limiting example, applying a square four pixel binning process 210 to an x-ray detector 300 having a native spatial resolution of a 70×70 micrometers pixel pitch, would form a frame corresponding to a spatial resolution at the detector of 140×140 micrometers. Applying a square sixty-four pixel binning process 210 (e.g., binning an 8×8 group of adjacent pixels) to an x-ray detector 300 having a native spatial resolution of a 70×70 micrometers pixel pitch, would form a frame corresponding to a spatial resolution at the detector of 560×560 micrometers. Non-square binning processes 210 can also be used. For instance, a 3×2 binning process 210 can be used such that the outputs of every three pixels are binned in a scanning direction and the outputs of every two pixels are combined in the orthogonal direction, the result is effective spatial resolution of 140×210 micrometers. Other binning combinations can be used. The binning process 210 can be performed in software, hardware, firmware, and combinations thereof. In examples, the binning process 210 can be used to expedite reading values from the x-ray detector 300. For instance, performing an 8×8 binning process 210 can include reading from the x-ray detector 300 by turning on eight sensor gates at a time to read values, such as by summing the values in a source direction or a charge direction. In many examples, the binning processes is summed in both the gates and source direction. In some examples, summation or averaging is performed in the source direction or charge direction.

The correction method 220 modifies an output (e.g., a charge result) from the x-ray detector 300 from the sensor based on the binning process 210. The correction method 220 allows for the binning process 210 to be variable and also allow for compatibility with legacy processes (e.g., legacy hardware, software or firmware designed to operate with a particular binning process). The compatibility is created by modifying the binned charge result from the binning process 210 prior to the use of the binned charge result as part of the mega pixel 230 used in a variety of ways, such as part of the AEC process. In an example, the correction method 220 treats the binning process 210 as having a default of 8×8 binning to preserve legacy compatibility for legacy systems and processes having a binning of 8×8. In this manner, the correction method 220 leaves the output unchanged (e.g., divides by one) when the binning process 210 performs 8×8 binning.

The illustrated correction method 220 includes operation 222, which determines a binning mode used in the binning process 210. The binning mode may be detected in any of a variety of ways, such as based on user input, based on one or more values obtained from the binning process 210 (e.g., a resolution thereof), metadata obtained from the binning process (e.g., metadata describing the binning performed), or via flags (e.g., software, hardware, or firmware flags). In the illustrated example there are there possible binning modes: 8×8, 2×2, and 1×1, though greater or fewer modes may be used. If 8×8 binning is used, the flow of the correction method 220 moves to operation 224 in which the image output is unmodified (e.g., divided by 1). If 2×2 binning is used, the flow of the correction method 220 moves to operation 226 in which the binned charge result from the sensor is divided by 4. If 1×1 binning is used, then the flow of the correction method 220 moves to operation 228 in which the binned charge result from the sensor is divided by 8. Following processing in operation 224, operation 226, or operation 228, the binned charge result from the binning process 210 then forms the mega pixel 230.

One or more mega pixels 230 can be used in a variety of ways, such as part of the AEC process to measure the densest part of the specimen to optimize the x-ray mAs used during actual imaging of the specimen. In AEC, the x-ray source 114 is energized to emit a short pulse of x-rays (sometimes known as a "scout pulse") that pass through a specimen and are received at the x-ray detector 300. An AEC frame is then read from the detector and used to calibrate the amount of radiation used to image the specimen. In an example, the resulting AEC frame is used in conjunction with a look up table to determine the correct amount of radiation to be used to image the specimen. The amount of radiation is expressed as milliampere-seconds (mAs), which is the amount of radiation produced (milliamperes) during an amount of time (seconds). In some examples, the following formula is used:

$$imaging_{mAs} = \frac{S \times (G \times k)}{I}$$

where $imaging_{mAs}$ is the mAs of radiation to be produced by the x-ray source for imaging the specimen; S is the mAs of radiation that was produced by the scout pulse; G is a desired exposure value (e.g., a value obtained by looking up a desired exposure in a dose table or manually entered by a clinician); k is a scaling factor used to calibrate the value G, and I is the readout from the detector as a result of the scout pulse. The resulting $imaging_{mAs}$ is used to determine the total mAs needed to appropriately image the specimen. The $imaging_{mAs}$ can then be used to determine a total amount of time to image the specimen based on the current of the x-ray source 114. In examples, the AEC can determine exposure parameters based on the scout pulse.

Figure 3:
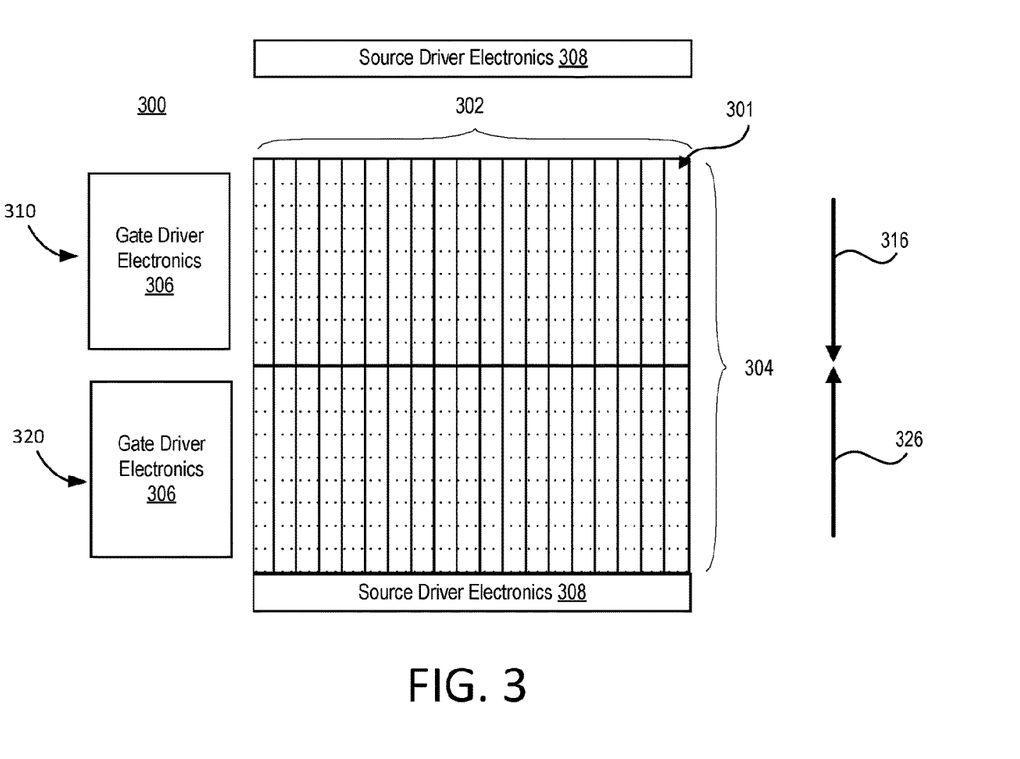
FIG. 3 illustrates an example block diagram of an x-ray detector.

FIG. 3 illustrates an example block diagram of the x-ray detector 300. In the illustrated example, the x-ray detector 300 includes a first portion 310 and a second portion 320. Both the first portion 310 and the second portion 320 include respective gate driver electronics 306 and source driver electronics 308. The x-ray detector 300 also includes source lines 302 and gate lines 304. Each source line 302 is coupled to the source driver electronics 308. Each gate line 304 is coupled to the gate driver electronics 306. The source lines 302 and the gate lines 304 divide the x-ray detector 300 into pixels 301. During x-ray exposure of the x-ray detector 300, the electric charge at each location of pixels 301 of the x-ray detector 300 is accumulated and stored. The electric charge relates to the number of photons received at the pixel 301 during the x-ray exposure. The electric charge is representative of the attenuation experienced by the individual transmitted x-rays as they travelled through the specimen being imaged. Following x-ray exposure, the electric charge pattern of the x-ray detector 300 is read out and converted to a digital image, which is referred to herein as a frame. The brightness of the individual pixels of the frame directly relates to the electronic charge of the pixels 301 and enables a visual representation of the structure of the imaged specimen. During readout, the gate lines 304 are sequentially accessed by the gate driver electronics 306, and the charge of a pixel 301 in each source line 302 of the accessed gate line 304 is sampled by the source driver electronics 308.

In an example, each pixel 301 embedded in a thin film transistor (TFT) of the x-ray detector 300 includes a capacitor and a field-effect-transistor (FET) switch. As x-rays impinge on the pixel 301, charge accumulates at the capacitor. Following x-ray exposure, the capacitor stores a charge representative of the x-ray attenuation at the location of the pixel 301. The charge stored on the capacitor is then transferred via the TFT switch to the charge integrator or charge amplifier electronics. The gate driver electronics 306 turns on the TFT pixel, transfer the stored charge on the TFT pixel storage capacitor to the x-ray charge amplifier integrator, the amplifier then converts the charge to voltage and send the voltage for digitization. This example process results in the creation of a frame as output from the x-ray detector 300. Other processes may also be used. The illustrated x-ray detector 300 is configured to read simultaneously from the first portion 310 and the second portion 320. Readings from the first portion 310 are performed in a first direction 316 (e.g., top to bottom) and the readings from the second portion 320 are performed in a second direction 326 (e.g., bottom to top). The technology need not be limited to a single readout direction. Example readout directions include inside-out readout, top-down readout, and bottom-up readout. During long exposure times (e.g., exposure times of at least 11 seconds), dark leakage currents associated with the x-ray detector 300 are not compensated fully, and a "virtual line" artifact is visible at a location in an output frame corresponding to the seam between the first portion 310 and the second portion 320 of the x-ray detector 300. Other artifacts may also be visible, such as an area of non-uniformity.

Figure 4:
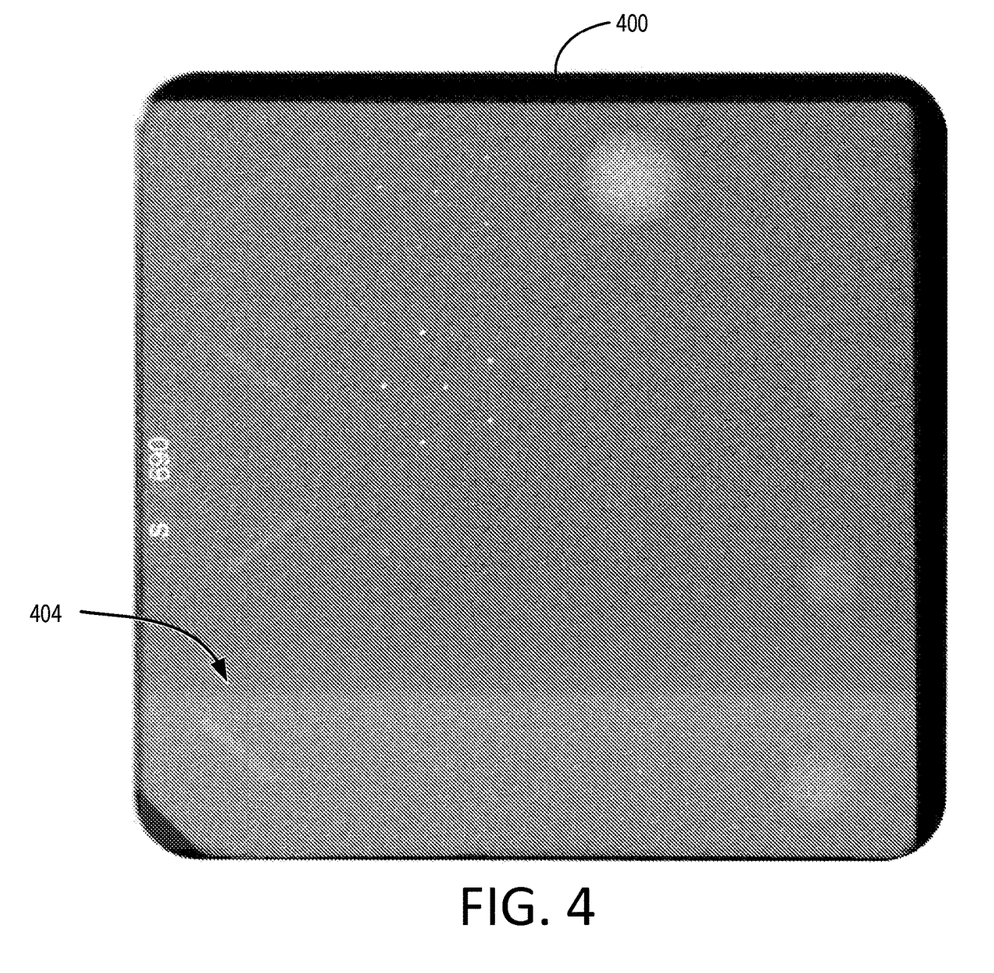
FIG. 4 illustrates an example output frame including a virtual line artifact.

FIG. 4 illustrates an example output frame 400 including a virtual line artifact 404. The virtual line artifact 404 is an elongate area of non-uniformity in the output frame 400. An area of non-uniformity is a visual artifact in the output frame 400 having characteristics that are not representative of the specimen being imaged. Such areas of non-uniformity can be the result of charge amplifier gain non-linearity and a length of exposure used to create the output frame 400. Areas of non-uniformity that are due to charge amplifier gain non-linearity typically appear as rectangles or lines associated with individual charge amplifier ASIC physical boundaries adjacent to one another. In many examples, the virtual line artifact 404 appears as a line running through the output frame 400 that is noticeably darker or lighter than nearby areas of the image. In many examples, the virtual line artifact 404 is the result of the use of a long exposure sequence.

Figure 5:
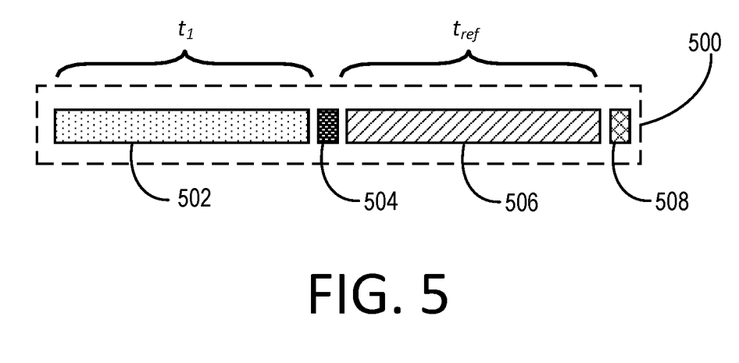
FIG. 5 illustrates an example long exposure sequence.
Figure 6:
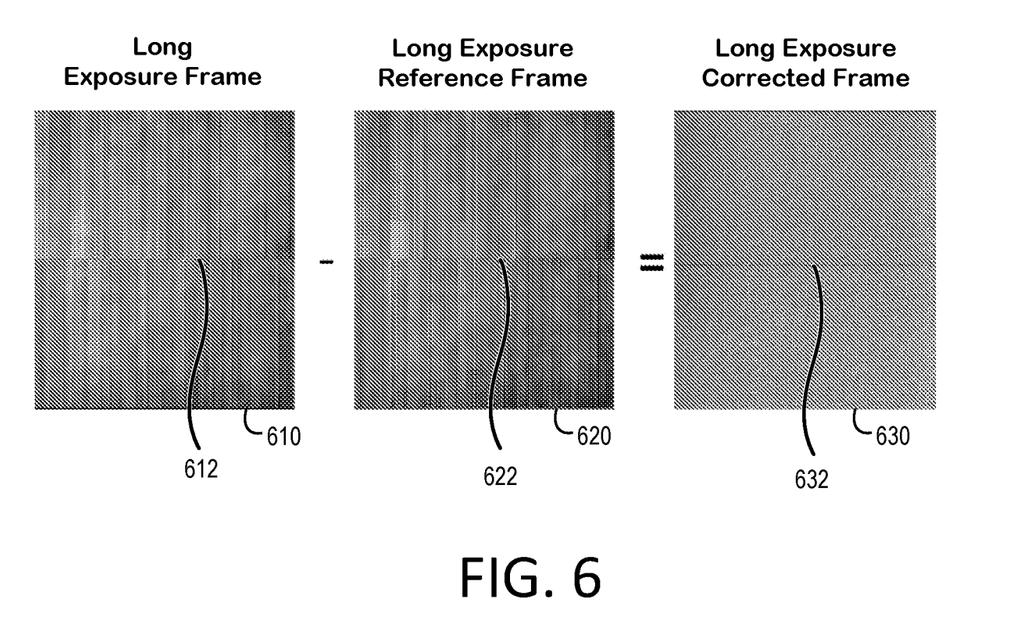
FIG. 6 illustrates the creation of a long exposure corrected frame from a long exposure frame and a long exposure reference frame.
Figure 7:
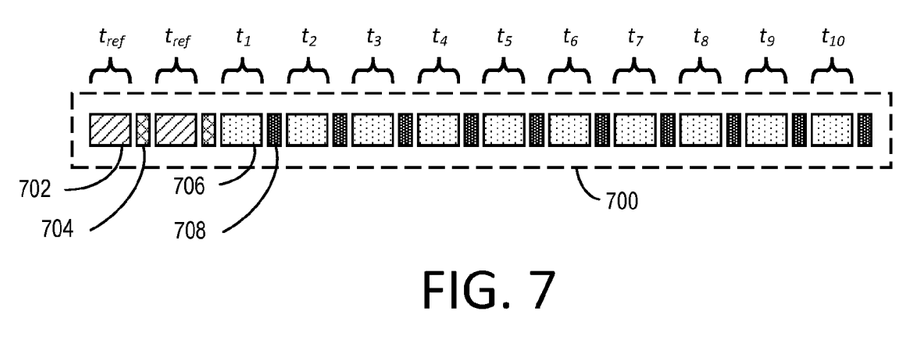
FIG. 7 illustrates an example exposure sequence.

In an example, the output frame 400 having the virtual line artifact 404 is the result of a long exposure sequence 500 as described in relation to FIG. 5 and the creation of a long exposure corrected frame 630 from a long exposure frame 610 and a long exposure reference frame 620 as described in FIG. 6. By contrast, FIG. 7 defines an exposure sequence 700 that presents an improvement over the exposure sequence 500 by mitigating the creation of a virtual line artifact. Unlike the single exposure window of the long exposure sequence 500, the exposure sequence 700 defines a plurality of exposure windows. And unlike the single reference window of the long exposure sequence 500, the exposure sequence 700 defines a plurality of reference windows. As will be discussed in more detail, the exposure sequence 700 presents advantages over the long exposure sequence relating to mitigating the formation virtual line artifacts 404. FIGS. 5-7 and the associated exposure sequences are discussed in more detail below.

FIG. 5 illustrates an example long exposure sequence 500 defining a long specimen exposure window 502, a long specimen readout window 504, a long reference exposure window 506, and a long reference readout window 508. The long specimen exposure window 502 is a window during which the x-ray source 114 is energized to image a specimen. The long specimen exposure window 502 has a duration of time $t_1$. The time $t_1$ may be selected to be sufficient to properly image the specimen. In an example, the time $t_1$ is selected based on an AEC process (e.g., as described above). In many examples, a long specimen exposure window 502 is considered "long" if the time $t_1$ is at least about eleven seconds, though other durations may be considered "long". In an example, a long specimen exposure window 502 is considered "long" if the time $t_1$ is the amount of time for which it is likely for an output frame to have at least one exposure duration-related visual artifact, such as a virtual line artifact.

The long specimen readout window 504 is a window during which the x-ray detector 300 is read to obtain a long exposure frame. Reading from the x-ray detector 300 can take a variety of forms, such as one described above. The long reference exposure window 506 is a window during which a reference frame is generated. A reference frame is a frame obtained to improve the quality of a resulting output frame by subtracting off an electronic structure pattern or noise pattern. In many examples, the long reference exposure window 506 is a window during which the x-ray detector 300 is left to expose without the x-ray source being energized. In other examples, the x-ray source is energized but the specimen is not present for imaging. The resulting frame can capture amplifier gain, flaws in the sensor, or other gain anomalies. The frame can then be used to create a gain map that can be used to correct for these anomalies in an exposure frame or otherwise be used to produce a higher-quality output frame. Such a process is described in greater detail below, such as in relation to FIG. 6 and FIG. 8. The long reference exposure window 506 has a duration of time $t_{ref}$. In many examples, the long reference exposure window 506 has a duration that matches the duration $t_1$ of the long specimen exposure window 502.

The long reference readout window 508 is a window during which the x-ray detector 300 is read to obtain a long exposure reference frame. In some examples, the long exposure sequence 500 does not include the long reference exposure window 506 and the long reference readout window 508. For instance, a reference frame may not be captured in the sequential order shown in FIG. 6. Although the long exposure sequence 500 is shown as having the long specimen exposure window 502 and the long specimen readout window 504 occur before the long reference exposure window 506 and the long reference readout window 508, their order may be reversed. In examples, the long exposure sequence 500 is stored in a data structure describing the long exposure sequence 500 in a machine-readable form usable by the controller 120 or another component of the radiographic imaging system 100 to cause the imaging of a specimen.

FIG. 6 illustrates the creation of a long exposure corrected frame 630 from a long exposure frame 610 and a long exposure reference frame 620. The long exposure frame 610 is a frame generated by imaging a specimen during a long-exposure window. For instance, the long exposure frame 610 may be generated from a radiographic imaging system 100 operating according to the long exposure sequence 500. In particular, the long exposure frame 610 may be generated by exposing the specimen during the long specimen exposure window 502 and reading detector data during the long specimen readout window 504. As illustrated, the long exposure frame 610 includes a virtual line artifact 612.

The long exposure reference frame 620 is a frame obtained to improve the quality of long exposure frame 610. The long exposure reference frame 620 may be generated from the radiographic imaging system 100 operating according to the long exposure sequence 500. In particular, the long exposure reference frame 620 may be generated during the long reference exposure window 506 and reading detector data during the long reference readout window 508. As illustrated, the subtraction of the long exposure reference frame 620 from the long exposure frame 610, includes a virtual line artifact 622, which may be caused as a result of the long exposure times.

The long exposure corrected frame 630 is a frame generated using the long exposure frame 610 and the long exposure reference frame 620. As illustrated, the long exposure corrected frame 630 is generated by subtracting the long exposure reference frame 620 from the long exposure frame 610. While the appearance of some artifacts are mitigated in the long exposure corrected frame 630, even after generating the long exposure corrected frame 630, a virtual line artifact 632 is still present. In view of the presence of the virtual line artifact 632 present in the long exposure corrected frame 630, it would be desirable to define an exposure sequence that can properly expose a specimen (e.g., satisfying a desired exposure time) while mitigating the presence of visual artifacts in the resulting frame.

FIG. 7 illustrates an example exposure sequence 700 that mitigates the presence of visual artifacts (e.g., particularly visual line artifacts) in a resulting frame. The exposure sequence 700 defines a plurality of reference exposure windows 702, a plurality of reference readout windows 704, a plurality of specimen exposure windows 706, and a plurality of specimen readout windows 708. Each of the specimen exposure windows 706 is a window during which the x-ray source 114 is energized to image a specimen. Each specimen exposure window 706 has an exposure time period of time $t_n$. In many examples, the exposure time periods for each of the specimen exposure windows 706 are substantially the same. In some examples, the exposure time periods of the specimen exposure windows 706 vary. The time $t_n$ may be such that a total of the exposure time periods satisfies a desired exposure time. The desired exposure time may be an exposure time sufficient to properly image the specimen. In an example, the desired exposure time is selected based on an AEC process, such as the one described above. In many examples, the exposure time period is sufficiently short as to mitigate the presence of a virtual line in an output frame resulting from the exposure sequence 700. Each of the plurality of specimen readout windows 708 is a window during which the x-ray detector 300 is read to obtain an exposure frame. During each of the plurality of specimen readout windows 708, the x-ray source 114 is not energized or the x-ray detector 300 is otherwise not exposed to x-ray energy.

Figure 8:
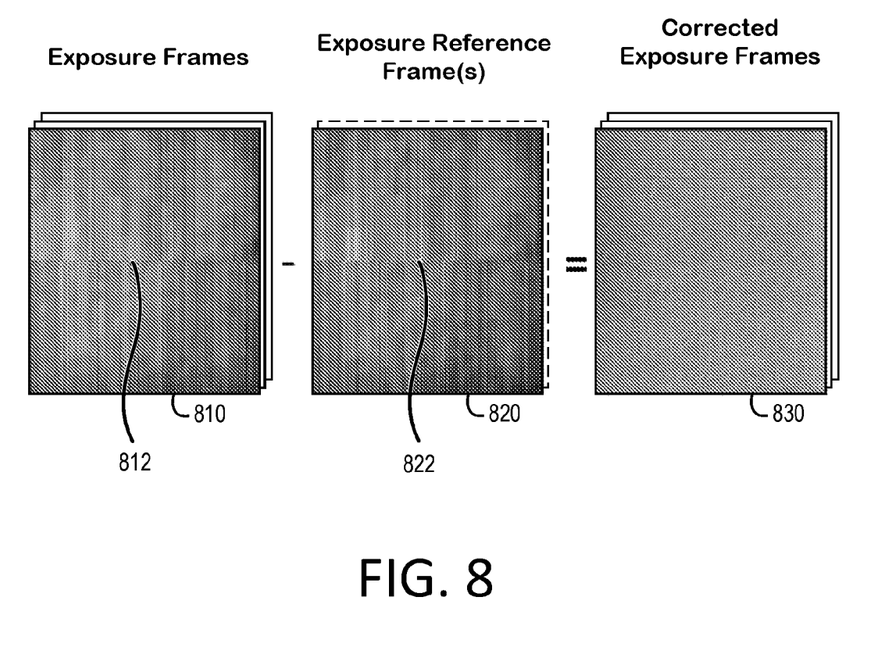
FIG. 8 illustrates the creation of one or more corrected exposure frames from a plurality of exposure frames and one or more exposure reference frames.

Each of the reference exposure windows 702 is a window during which a reference frame is generated. In many examples, each of the reference exposure windows 702 is a window during which the x-ray detector 300 is left to expose without the x-ray source being energized. This can allow the generation of a reference frame that captures background noise, flaws in the x-ray detector 300, or other anomalies. The reference frame can be used to create a gain map for correcting anomalies in an exposure frame or otherwise be used to produce a higher-quality output frame. The exposure reference frame 820 can be subtracted off of the exposure frame 810 or otherwise be used to produce a higher-quality output frame. Each reference exposure window 702 has a duration of time $t_{ref}$. In many examples, the reference exposure window 702 has a duration that matches the duration $t_n$ of one or more of the specimen exposure windows 706, and the total duration of the reference exposure windows 702 (e.g., the total amount of time of all reference exposure windows 702) is less than a total duration of all specimen exposure windows 706 (e.g., the total amount of time of all specimen exposure windows 706). Having the total duration of the reference exposure windows 702 be less than a total duration of the specimen exposure windows 706 can advantageously reduce an overall imaging time. In an example, there is a minimum exposure time of 7.00 seconds, and image display computation starts approximately 9.36 seconds after the initiation on an exposure sequence using multiple, shorter exposure windows. By contrast, having a single longer reference exposure window and a single longer specimen exposure window could result in display image computation beginning approximately 14.16 seconds after the exposure initiation of the 7.00 seconds of exposure. In an example, a minimum exposure time of 7.00 seconds has 8.40 seconds of total exposure window time using an exposure sequence having approximately 0.96 seconds of total charge readout time, two reference exposure frames, and ten exposure frames. On the other hand a 7.00 second exposure would take approximately 14.00 seconds of total exposure window time using an exposure sequence having a single exposure, a single reference exposure, and approximately 0.16 second charge readout time.

In the illustrated example, there are a plurality of reference exposure windows 702. In some examples each of the multiple reference exposure windows 702 is substantially identical. The plurality of reference exposure windows 702 can be used to increase the quality of the resulting frames. In an example, the plurality of reference exposure windows 702 can be averaged or otherwise combined in order to produce an improved reference exposure frame for use in correcting the exposure frame. The reference readout window 704 is a window during which the x-ray detector 300 is read to obtain an exposure reference frame.

In the illustrated example, the plurality of reference exposure windows 702 occur before the plurality of specimen exposure windows 702. In some instances, such a configuration can beneficially reduce an overall wait time for a user to view an output image created using the exposure sequence 700.

In some examples, the exposure sequence 700 does not include the reference exposure window 702 and the reference readout window 704. For instance, a reference frame may not be captured in the sequential order shown in FIG. 7. Although the exposure sequence 700 is shown as having the plurality of specimen exposure windows 706 and the plurality of specimen readout window 708 occur after the plurality of reference exposure windows 702 and the plurality of reference readout windows 704, their order may be reversed. In some examples, one or more of the plurality of reference exposure windows 702 and one or more of the associated reference readout windows 704 may occur between two or more sets of specimen exposure windows 706 and associated specimen readout windows 708. In examples, the exposure sequence 700 is stored in a data structure describing the exposure sequence 700 in a machine-readable form usable by the controller 120 or another component of the radiographic imaging system 100 to cause the imaging of a specimen.

FIG. 8 illustrates a method of generating one or more corrected exposure frames 830 from a plurality of exposure frames 810 and one or more exposure reference frames 820. The plurality of exposure frames 810 and the one or more exposure reference frames 820 are created according to an exposure sequence, such as the exposure sequence 700 of FIG. 7. The corrected exposure frames 830 lack a substantial virtual line artifact, which may otherwise be present in the plurality of exposure frames 810 and the one or more exposure reference frames 820. The one or more corrected exposure frames 830 can be created in a variety of ways. In some examples, each of the exposure frames 810 are corrected with one or more respective exposure reference frames 820 to create the plurality of corrected exposure frames 830. In some examples, correcting each of the exposure frames 810 includes correcting each of the exposure frames 810 with an average reference frame created by averaging two or more exposure reference frames 820. In some examples, the exposure frames 810 are combined (e.g., by summing the plurality of exposure frames 810) before being modified by the one or more exposure reference frames 820 or combinations of exposure reference frames 820. In some examples, the plurality of corrected exposure frames 830 are generated prior to being combined (e.g. by summing the plurality of corrected exposure frames 830 to form a single corrected exposure frame 830 for output or additional processing).

Each of the plurality of exposure frames 810 is a frame generated by imaging a specimen during a respective one of a plurality of specimen exposure windows 706. For instance, each of the plurality of exposure frames 810 may be generated from a radiographic imaging system (e.g., the radiographic imaging system 100) operating according to the exposure sequence. In particular, the each of the plurality of the exposure frames 810 may be generated by exposing the specimen during a respective each of a plurality of specimen exposure windows and reading detector data during a respective one of a plurality of specimen readout windows. As illustrated, each of the plurality of exposure frames 810 includes a virtual line artifact 812. In some examples, the exposure frames 810 lack a virtual line artifact 812 due to the shortness of the length of time $t_n$. In other examples, the exposure frames 810 still have a virtual line artifact 812, but the virtual line artifact 812 is mitigated (e.g., made faint or small enough) such that it is substantially absent from a resulting corrected exposure frame 830 or absent when multiple exposure reference frames 820 are combined.

Each of the one or more exposure reference frames 820 is a frame obtained to improve the quality of the one or more resulting corrected exposure frames 830. The exposure reference frame 820 may be generated from the radiographic imaging system 100 operating according to the exposure sequence. In particular, the exposure reference frame 820 may be generated during a reference exposure window and reading detector data during a reference readout window. As illustrated, the exposure reference frame 820 includes a virtual line artifact 822. In some examples, the exposure reference frames 820 lack a virtual line artifact 822 due to the shortness of the length of both time $t_{ref}$ and time $t_n$. In other examples, the exposure reference frames 820 still have a virtual line artifact 822, but the virtual line artifact 822 is usable to correct a matching virtual line artifact 812 in the exposure frame 810. In other examples, the virtual line artifact 822 is inconsequential enough to be absent from a corrected exposure frame resulting from the exposure frames 810 being corrected by the one or more exposure reference frame 820.

The corrected exposure frame 830 is a frame generated using the exposure frame 810 and the exposure reference frame 820. As illustrated, the corrected exposure frame 830 is generated by subtracting the exposure reference frame 820 from the exposure frame 810. As illustrated, after generating the corrected exposure frame 830, a virtual line artifact is absent from the corrected exposure frame 830 despite a total time of specimen exposure windows otherwise being sufficient to cause a virtual line artifact.

Figure 9:
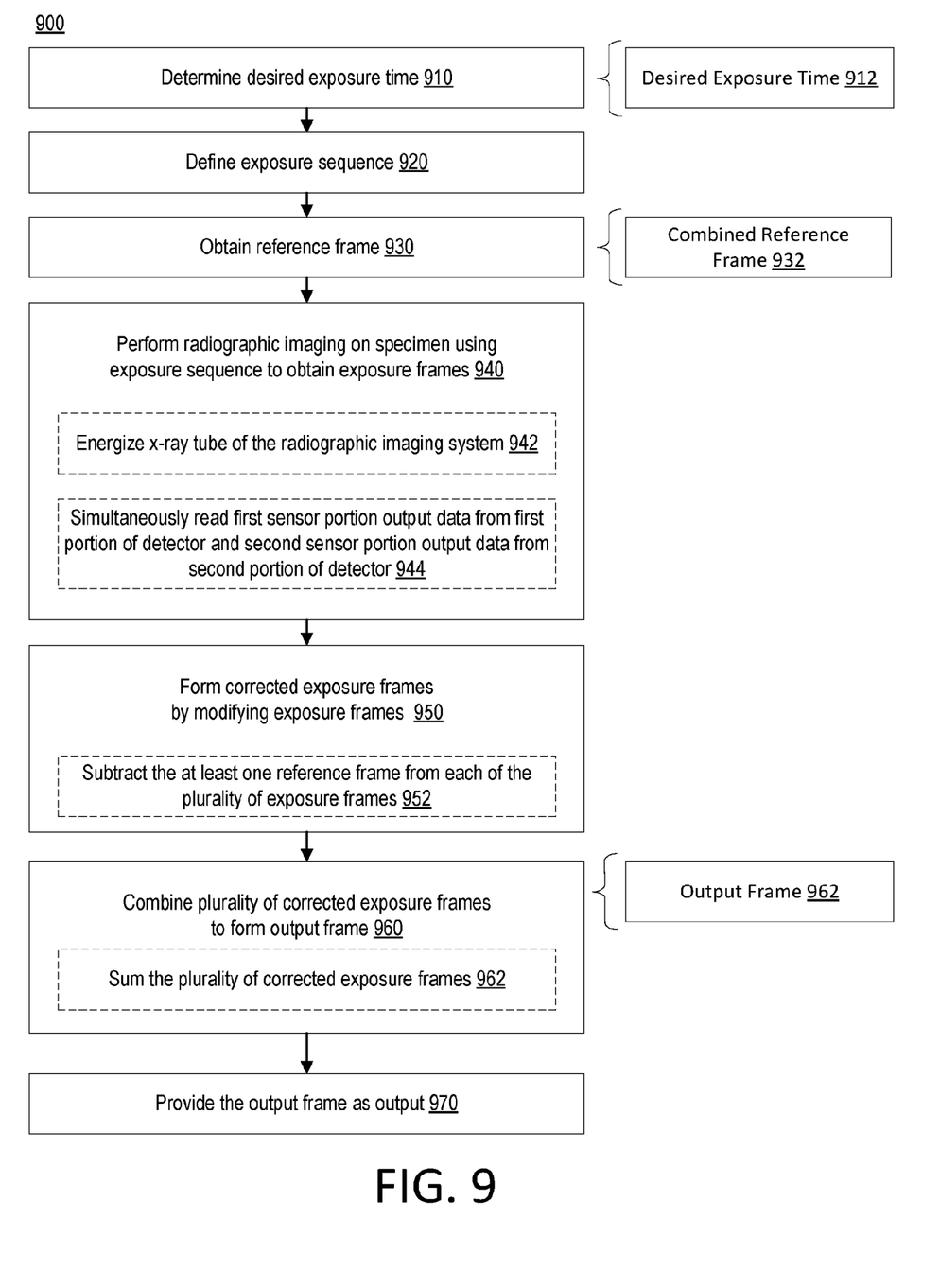
FIG. 9 illustrates an example method for radiographic imaging.

FIG. 9 illustrates an example method 900 for radiographic imaging. In an example, instructions for performing one or more operations of method 900 are stored on a computer-readable medium (e.g., the memory 124 of FIG. 1). In an example, the instructions are executed by a processor (e.g., the processor 122), which causes the performance of the method 900.

The example method 900 includes operation 910. Operation 910 includes determining a desired exposure time 912. The desired exposure time 912 can be determined in any of a variety of ways. In an example, the desired exposure time 912 is obtained directly from a clinician (e.g., via an input device, such as the input device 128 of FIG. 1). In another example, the desired exposure time 912 is calculated by a radiographic imaging system (e.g., the controller 120 of the radiographic imaging system 100 of FIG. 1). For instance, the radiographic imaging system includes instructions for calculating the desired exposure time 912 using a result of an AEC process.

Operation 920 includes defining an exposure sequence (e.g., the exposure sequence 700 of FIG. 7). The exposure sequence can be defined in any of a variety of ways. In an example, the exposure sequence is partially or entirely defined by the clinician (e.g., from input received via an input device). In an example, the radiographic imaging system automatically defines the exposure sequence based on the desired exposure time. For instance, a controller (e.g., the controller 120 of FIG. 1) defines the exposure sequence. In an example, defining the exposure sequence includes determining a number of reference exposure windows to define (e.g., zero or more reference exposure windows), determining a number of exposure windows to define (e.g., two or more specimen exposure window and specimen readout window sets), and determining an exposure time period of each of the exposure windows. In an example, the number and length of the exposure windows is determined based on the desired exposure time 912 such that the exposure time period of each of the exposure windows is less than an amount of time that is predicted to result in an area of non-uniformity in an output frame (e.g., a virtual line artifact 404 as in FIG. 4). In an example, the desired exposure time 912 is between 7.0 seconds and 20.0 seconds, and the radiographic imaging system defines an exposure sequence having ten exposure windows, each having an exposure time of between 0.7 seconds and 2.0 seconds. In many examples, the exposure windows each have a same exposure time. In some examples, two or more exposure windows have different exposure times. In an example, defining the exposure sequence further includes determining an ordering of the exposure sequence (e.g., whether reference frames are obtained before or after the exposure frames).

Operation 930 includes obtaining at least one exposure reference frame (e.g., an exposure reference frame 820 as described in relation to FIG. 8). The exposure reference frame can be obtained in any of a variety of ways. In an example, the exposure reference frame is a previously-taken averaged reference frame. For instance, exposure one or more exposure reference frames may be periodically generated and stored for later use (e.g., as part of a maintenance or calibration procedure for the radiographic imaging system). In such examples, obtaining the at least one exposure reference frame includes obtaining the at least one exposure reference frame from storage (e.g., from memory 124 of the radiographic imaging system 100 of FIG. 1). The use of a previously-taken reference frame can advantageously decrease a total amount of imaging time needed by obviating the need to obtain a reference frame. In many examples, obtaining the at least one exposure reference frame includes obtaining at least one reference frame concomitant to imaging a specimen. This can include obtaining the exposure reference frame by following an exposure sequence defining one or more windows for obtaining and reading out an exposure reference frame. In some examples, both a previously-taken reference frame and a concomitant reference frame are used. For instance, a previously-taken reference frame can be used to modify one or more reference frames to provide a preview to a clinician while a concomitant reference frame is obtained. Once the concomitant reference frame is obtained, the concomitant reference frame can be used in place of the previously-taken reference frame. In some examples, the operation 930 includes combining a plurality of exposure reference frames to form a combined exposure reference frame 932. The combined exposure reference frame 932 can be formed by, for example, averaging the plurality of exposure reference frames. Once obtained, the exposure reference frame and/or the combined exposure reference frame 932 is stored in short or long-term storage for later use.

Operation 940 includes performing radiographic imaging on a specimen using an exposure sequence (e.g., the exposure sequence 700) to obtain exposure frames. Performing radiographic imaging can take a variety of forms. In many examples, a controller (e.g., the controller 120 of FIG. 1) controls an x-ray source (e.g., the x-ray source 114 of FIG. 1) and an x-ray detector (e.g., the x-ray detector 300 of FIG. 3) using the exposure sequence to image the specimen, resulting in two or more exposure frames. In an example, operation 940 includes operation 942 and/or operation 944. Operation 942 includes energizing an x-ray tube of the radiographic imaging system. In an example, the controller causes current to be provided to the x-ray source to cause the x-ray source to emit x-rays toward the specimen. Operation 944 includes simultaneously reading a first sensor portion output data from a first portion of the x-ray detector and second sensor portion output data from a second portion of the x-ray detector. In an example, each exposure frame is based on first sensor portion output data and second sensor portion output data. For instance, the controller uses the first sensor portion output data to form the top portion of an exposure frame and the second sensor portion output to form the bottom portion of the exposure frame.

Operation 950 includes forming one or more corrected exposure frames by modifying the plurality of exposure frames. In many examples, forming the one or more corrected exposure frames includes modifying each of the plurality of exposure frames with one or more of the exposure reference frames obtained in operation 930. In some examples, forming the one or more corrected exposure frames includes selecting one or more of the one or more exposure reference frames obtained in operation 930. For instance, a most-recently-taken exposure reference frame may be selected. The exposure reference frame may be selected based on a characteristic of the exposure reference frame. For instance, an exposure reference frame may be selected based on the reference frame having a similar exposure time to one or more of the exposure frames to be modified.

The exposure frames may be modified in any of a variety of ways. In an example, operation 950 includes operation 952, which includes subtracting at least one exposure reference frame from each of the plurality of exposure frames. This can include subtracting corresponding pixel values of the exposure reference frame from the exposure frame. For instance, the exposure frame and the exposure reference frame may be stored in an image format (e.g., bitmap, portable, network graphics, or another image format) that stores pixels as 16 bit values in an x-y coordinate format. The exposure frame may have a pixel value of (200) stored in the x-y coordinate (128, 128), and the exposure reference frame may have a pixel value of (50) stored in its x-y coordinate (128, 128). Subtracting the exposure reference frame from the exposure frame would result in a corrected exposure frame having value of (150) in its x-y coordinate (128, 128). In examples, pixel values are prevented from being negative (e.g., a value of zero is used instead of a negative number).

Operation 960 includes combining the plurality of corrected exposure frames to form the output frame 964. This operation 960 may also be referred to as "stacking" the corrected exposure frames. The corrected exposure frames may be combined in any of a variety of ways, such as averaging or summing the plurality of corrected exposure frames. In an example, operation 960 includes operation 962. Operation 962 includes summing the plurality of corrected exposure frames. This can include adding corresponding pixel values of each of the plurality of corrected exposure frames. For instance, a first of the plurality of exposure frames may have a pixel value of (200) stored in the x-y coordinate (128, 128), and a second of the plurality of exposure frames may have a pixel value of (50) stored in its x-y coordinate (128, 128). Adding the first and second corrected exposure frames would result in an output frame having a value of (250) in its x-y coordinate (128, 128). In an example, summing the plurality of corrected exposure frames includes summing pixel values of respective pixels of the plurality of corrected exposure frames to form a respective summed pixel in the output frame.

Depending on the number of exposure frames to be summed and their pixel values, the summing process may result in pixel values clipping or overflowing maximum possible values. For instance, where the pixel value is stored in 14 bits, there is a range of possible values of each pixel of 0 to 16,383. Summing ten pixels each having a value of 16,383 in a stack would result in the value of 163,830, which is higher than the maximum possible value of 65,536 for a 16-bit storage register. Various techniques can be used to address this challenge. For instance, the pixel values can be summed at a higher bit depth (e.g., 32-bits) that allows for the pixel values to be summed without clipping. Once the plurality of corrected exposure frames are summed, the pixel values can be scaled to a desired bit depth for storage or display. Although the output frame 964 is shown as being created by first correcting the exposure frames and then combining the corrected exposure frames, the process need not be limited to that order. For instance, the exposure frames may be combined first and then corrected to form a single corrected exposure frame that is also the output frame 964.

Operation 970 includes providing the output frame 964 as output. In an example, the output frame 964 is provided for display to a clinician at a display (e.g., the display 126 of FIG. 1). In another example, the output frame 964 is provided for storage at a network drive connected to the controller 120 over a network (e.g., the network 132 of FIG. 1).

This disclosure describes some examples of the present technology with reference to the accompanying drawings, in which only some of the possible examples were shown. Other aspects can, however, be embodied in many different forms and should not be construed as limited to the examples set forth herein. Rather, these examples were provided so that this disclosure was thorough and complete and fully conveyed the scope of the possible examples to those skilled in the art.

Although specific examples were described herein, the scope of the technology is not limited to those specific examples. One skilled in the art will recognize other examples or improvements that are within the scope of the present technology. Therefore, the specific structure, acts, or media are disclosed only as illustrative examples. Examples according to the technology may also combine elements or components of those that are disclosed in general but not expressly exemplified in combination, unless otherwise stated herein. The scope of the technology is defined by the following claims and any equivalents therein.

The invention claimed is:

1. A radiographic imaging system comprising:
   a specimen holder;
   an x-ray source;
   an x-ray detector, wherein the x-ray detector is configured to simultaneously output a first reading from a first portion of the x-ray detector and second reading from a second portion of the x-ray detector; and
   a controller comprising at least one processor and memory storing instructions that, when executed by the at least one processor, cause the radiographic imaging system to perform a set of operations comprising:
      determining a desired exposure time;
      defining an exposure sequence having a plurality of specimen exposure windows, wherein each specimen exposure window of the plurality of specimen exposure windows has an exposure time period, and wherein a total of the exposure time periods of the plurality of specimen exposure windows satisfies the desired exposure time;

controlling the x-ray source and the x-ray detector to obtain at least one exposure reference frame;
controlling the x-ray source and the x-ray detector using the exposure sequence to obtain a plurality of exposure frames from the x-ray detector;
forming a plurality of corrected exposure frames by modifying the plurality of exposure frames using the at least one exposure reference frame;
summing the plurality of corrected exposure frames to form an output frame; and
providing the output frame as output.

2. The radiographic imaging system of claim 1, wherein the set of operations further includes binning a group of pixels of the x-ray detector.

3. The radiographic imaging system of claim 2, wherein the set of operations further includes selectively modifying a size of the group of pixels on which the binning is performed.

4. The radiographic imaging system of claim 1, further comprising a display, wherein the set of operations includes providing the output frame as output using the display.

5. The radiographic imaging system of claim 1, wherein the x-ray source is configured to operate with a current of less than 1.5 milliamps.

6. The radiographic imaging system of claim 1, wherein the x-ray source is stationary.

7. The radiographic imaging system of claim 1, wherein the at least one exposure reference frame comprises at least two exposure reference frames;
wherein the set of operations further includes forming a combined exposure reference frame from the at least two exposure reference frames; and
wherein modifying the plurality of exposure frames using the at least one exposure reference frame comprises subtracting the combined exposure reference frame from each of the plurality of exposure frames.

8. The radiographic imaging system of claim 1, wherein forming the plurality of corrected exposure frames comprises:
subtracting the at least one exposure reference frame from each of the plurality of exposure frames.

9. The radiographic imaging system of claim 1, wherein summing the plurality of corrected exposure frames to form an output frame includes summing pixel values of respective pixels of the plurality of corrected exposure frames to form a respective summed pixel in the output frame.

10. A method for performing radiographic imaging, the method comprising:
determining, using a controller of an x-ray imaging system, a desired exposure time;
defining, using the controller of the x-ray imaging system, an exposure sequence having a plurality of specimen exposure windows, wherein each specimen exposure window of the plurality of specimen exposure windows has an exposure time period, and wherein a total of the exposure time periods of the plurality of specimen exposure windows satisfies the desired exposure time;
controlling, using the controller of the x-ray imaging system, an x-ray source and an x-ray detector of the x-ray imaging system to obtain at least one exposure reference frame;
controlling, using the controller of the x-ray imaging system, the x-ray source and the x-ray detector to perform radiographic imaging using the exposure sequence to obtain a plurality of exposure frames from the x-ray detector;
forming, using the controller of the x-ray imaging system, a plurality of corrected exposure frames by modifying the plurality of exposure frames using the at least one exposure reference frame;
summing, using the controller of the x-ray imaging system, the plurality of corrected exposure frames to form an output frame; and
providing, using the controller of the x-ray imaging system, the output frame as output.

11. The method of claim 10,
wherein forming the plurality of corrected exposure frames comprises:
subtracting the at least one exposure reference frame from each of the plurality of exposure frames.

12. The method of claim 10,
wherein the at least one exposure reference frame comprises at least two exposure reference frames;
wherein the method further comprises forming a combined exposure reference frame from the at least two exposure reference frames; and
wherein forming the plurality of corrected exposure frames comprises subtracting the combined exposure reference frame from each of the plurality of exposure frames.

13. The method of claim 10, wherein obtaining the at least one exposure reference frame includes obtaining the at least one exposure reference frame from a radiographic imaging system.

14. The method of claim 10, wherein obtaining the at least one exposure reference frame occurs before performing the radiographic imaging on the specimen.

15. The method of claim 10,
wherein the desired exposure time is at least 11.0 seconds; and
wherein performing the radiographic imaging comprises energizing an x-ray source of the radiographic imaging system with a current of less than 1.5 milliamps.

16. The method of claim 10,
wherein the desired exposure time is between 7.0 seconds and 20.0 seconds; and
wherein the exposure time period of each specimen exposure window of the plurality of specimen exposure windows is between 0.7 seconds and 2.0 seconds.

17. The method of claim 10, wherein performing the radiographic imaging comprises performing radiographic imaging on a breast tissue specimen.

18. The method of claim 10,
wherein performing the radiographic imaging comprises:
simultaneously reading first sensor portion output data from a first portion of an x-ray detector of the radiographic imaging system and second sensor portion output data from a second portion of the x-ray detector; and
wherein at least one of the plurality of exposure frames includes the first sensor portion output data and the second sensor portion output data.

19. The method of claim 10, further comprising:
performing, using the controller of the x-ray imaging system, radiographic imaging to obtain a long exposure frame having an exposure time of more than ten seconds from the radiographic imaging system;
obtaining, using the controller of the x-ray imaging system, a long exposure reference frame; and
forming, using the controller of the x-ray imaging system, a long exposure corrected frame using the long exposure frame and the long exposure reference frame, wherein the long exposure corrected frame comprises a virtual line artifact.

20. A non-transitory computer-readable medium comprising instructions that, when executed by one or more processors, cause the performance of a method as in claim 10.

* * * * *